United States Patent [19]

Nakano et al.

[11] Patent Number: 4,914,198

[45] Date of Patent: Apr. 3, 1990

[54] NOVEL SUBSTANCE UCY1003 AND PROCESS FOR PREPARING THE SAME

[75] Inventors: Hirofumi Nakano; Mitsunobu Hara; Yoshinori Yamashita, all of Machida; Isao Kawamoto, Hiratsuka; Katsuhiko Ando, Machida; Hiroshi Sano, Machida; Toru Yasuzawa, Machida; Katsuichi Shuto, Shizuoka, all of Japan

[73] Assignee: Kyowa Hakko Kogyo Co., Ltd., Tokyo, Japan

[21] Appl. No.: 946,842

[22] Filed: Dec. 29, 1986

[30] Foreign Application Priority Data

Dec. 26, 1985 [JP] Japan .................................. 60-294884

[51] Int. Cl.$^4$ .......................... C07J 71/00; C12N 1/14
[52] U.S. Cl. ...................................... 540/62; 540/933; 540/93; 540/254
[58] Field of Search ................. 260/397.2; 435/52, 53, 435/933, 171, 119; 540/93, 62

[56] References Cited

U.S. PATENT DOCUMENTS 3,230,240  1/1966  Godtfredsen .......................... 435/52

OTHER PUBLICATIONS

Turner, W. B., Fungal Metabolites 1971, Academic Press, pp. 262–267.

Primary Examiner—Charles F. Warren
Assistant Examiner—Irene Marx
Attorney, Agent, or Firm—Antonelli, Terry & Wands

[57] ABSTRACT

Novel substance UCY1003 produced by culturing of a microorganism has the following chemical structure and analgesic, hypotensive and antifungal activities:

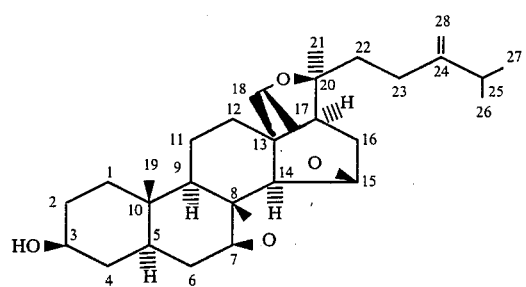

2 Claims, 4 Drawing Sheets

NOVEL SUBSTANCE UCY1003 AND PROCESS FOR PREPARING THE SAME

BACKGROUND OF THE INVENTION

The present invention relates to a novel compound UCY1003 having an analgesic activity, hypotensive activity and antifungal activity, and a process for preparing the same by fermentation.

The present inventors have made screening of microorganisms producing a substance with a useful pharmacological activity and have found that a microorganism belonging to the genus Penicillium isolated from fallen leaves of a Saghalien spruce growing in Onuma Park, Hokkaido, produces a substance having analgesic activity, hypotensive activity and antifungal activity. As a result of further investigations, the present inventors have successfully isolated and purified an active substance UCY1003 and have confirmed from its physicochemical properties that UCY1003 is a novel substance, and thus the present invention has been established.

It has also been clarified from elemental analysis, mass spectrum, IR spectrum, NMR spectrum and other physicochemical properties of UCY1003 that UCY1003 is a substance having a cholesterol skeleton specified by the chemical structure described hereinafter.

Triamcinolone, methylprednisolone and dexamethasone have been known as steroid substances having analgesic activity [Igaku no Ayumi (Development of Medical Science), 139(1), 41 (1986) published by Ishiyaku Shuppan Co., Ltd.].

Further, more than 20 substances have been known as steroid substances having antibacterial or antifungal activity (CRC Handbook of Antibiotic Compounds vol. VI p. 149, 1981 CRC Press, U.S.A.).

UCY1003 is quite different from the above known steroid substances in having a bridging oxygen between 7- and 8-positions, 15- and 18-positions, and 18- and 20-positions, respectively, as is apparent from the structure described hereinafter.

SUMMARY OF THE INVENTION

Novel compound UCY1003 of the present invention having analgesic, hypotensive and antifungal activities is specified by the following physicochemical properties:

(a) Molecular formula: $C_{28}H_{42}O_4$
(b) Elemental analysis: C: 75.97%, H: 9.56%, N: 0%
(c) Molecular weight: molecular weight of UCY1003 measured by EI mass spectrum method is 442, and the mass spectrum is shown in FIG. 1 (EI method)
(d) Melting point: 198.9° C.
(e) Specific rotation: $[\alpha]_D^{25} = -60.8°$ (C 1.0, CHCl$_3$)
(f) Ultraviolet absorption spectrum: only terminal absorption is shown
(g) Infrared absorption spectrum: shown in FIG. 2 (KBr method)
(h) PMR spectrum: shown in FIG. 3 (in CDCl$_3$)
(i) CMR spectrum: shown in FIG. 4 (in CDCl$_3$)
(j) Solubility: readily soluble in methanol, ethanol, chloroform and acetone; soluble in ethyl acetate, toluene and water; and sparingly soluble in hexane
(k) State of the substance: white needles, neutral substance
(l) Color reaction: positive to iodine reaction It was determined from elemental analysis, infrared absorption spectrum, PMR spectrum, CMR spectrum and other physicochemical properties of UCY1003 that UCY1003 has the following structure:

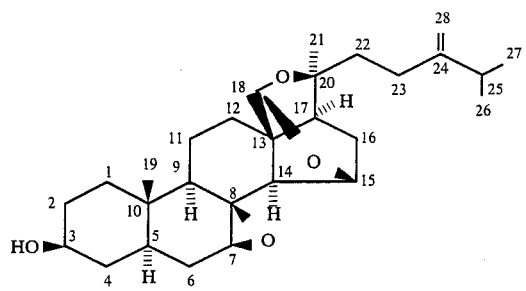

UCY1003 can be prepared by culturing a UCY1003-producing strain of the genus Penicillium.

BRIEF DESCRIPTION OF THE DRAWINGS

In FIG. 1, portions of mass higher than * are represented with 5-fold sensitivity.

DETAILED DESCRIPTION OF THE INVENTION

Figure 1:
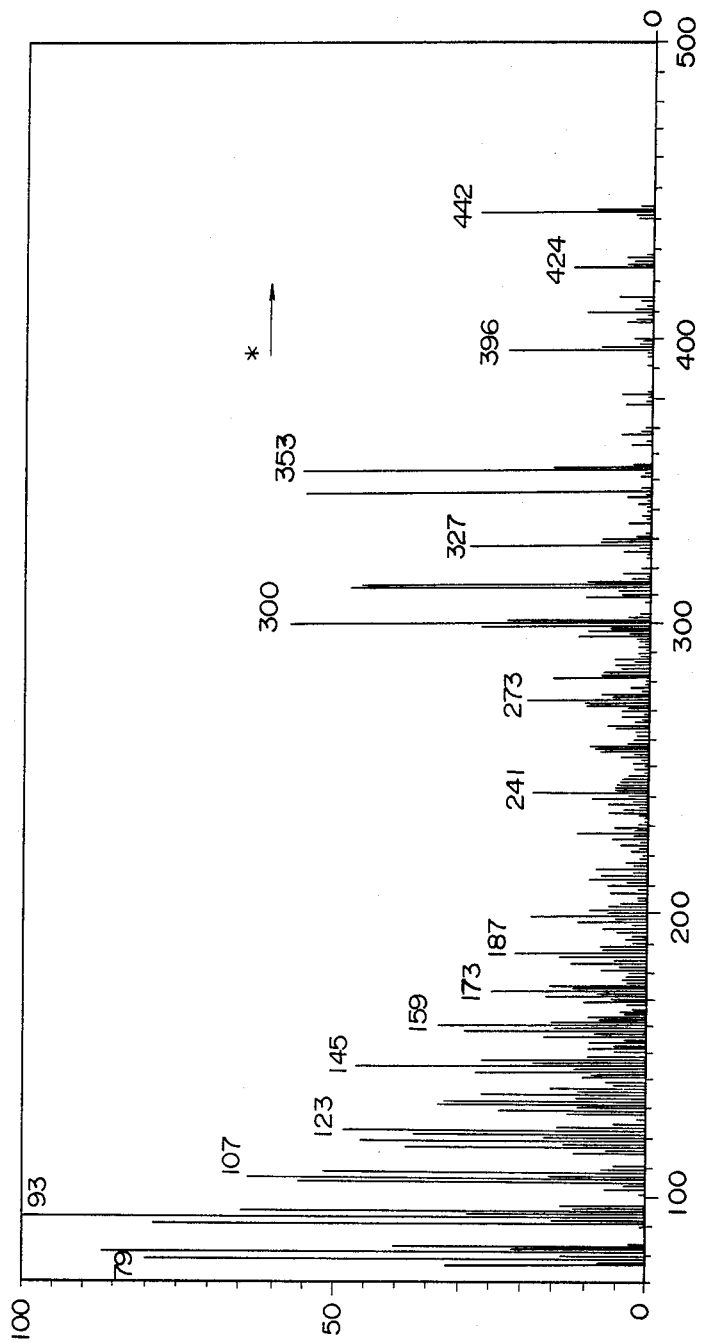
FIGS. 1 to 4 show mass spectrum (EI method), infrared absorption spectrum (KBr method), PMR spectrum (in CDCl$_3$) and CMR spectrum (in CDCl$_3$) respectively, of UCY1003.

UCY1003 can be obtained by culturing a UCY1003-producing strain belonging to the genus Penicillium in a nutrient medium, and recovering UCY1003 from the culture broth. Any strain can be used as a UCY1003-producing strain, so long as it is a strain belonging to the genus Penicillium and having an ability to produce UCY1003.

Further, some mutant strains of these strains obtained by treatment with a mutagen or by spontaneous generation can produce UCY1003, and can also be used in the present invention.

Typical strain is strain KAC-1843 isolated from fallen leaves of a Saghalien spruce growing in Hokkaido by the present inventors. Microbiological properties of the strain KAC-1843 are as follows:

(1) Growth on various media (1) Czapek yeast autolysate agar (Pitt, 1973)

The strain shows good growth when cultured at 25° C. Diameters of colonies reach 4–4.5 cm by culturing for 7 days. Radiate striations are observable on the colony surfaces. The colony surfaces ar yellow at the center, turn grey and then blue toward the periphery, and white at the periphery. Radiate striations are observable on the back sides of colonies, and the back sides are orange. Pale yellow pigments are secreted in the agar medium. Growth is slow when culturing is carried out at 5° C. Diameters of colonies are 3 mm after culturing for 7 days. The colony surfaces are raised fluffily and white. The back sides are orange. No growth is observed when culturing is carried out at 37° C.

(2) Malt extract agar

Good growth is observed, and diameters of colonies reach 3.5–4 cm by culturing at 25° C. for 7 days. The colony surfaces are bluish green at the center and white at the periphery. The back sides are pale yellowish white. No radiate striations are observable on the colonies.

(3) 25% Glycerol nitrate agar (Pitt, 1973)

Growth is a little slow, and diameters of colonies reach 1.5–2 cm by culturing at 25° C. for 7 days. The colony surfaces are yellowish white at the center and bluish white toward the periphery. The back sides are yellow. Radiate striations are observable on the surfaces and the back sides of the colonies.

(2) Morphological characteristics

Mycelia are hyaline, septate, and well branched. Penicillus type is of biverticillate-symmetrical. Conidia are subspheroidal, and 1.5–3 μm in diameter. The chain of conidia extends up to 30 μm. Phialides are ampulliform, closely packed in verticils of 8 to 12, 6.5–9 μm long and 2–2.5 μm wide. Metulae are 9–11 μm long and 2–4.5 μm wide. Conidiophores directly arise from hyphae and 450–700 μm long. Conidiophores, metulae, phialides and conidia are all smooth.

From the results of the foregoing observations, the present microorganism has been identified as *Penicillium paxilli*. Microbiological properties of *Penicillium paxilli* are described in detail in Pitt: "The genus Penicillium and its teleomorphic status Eupenicillium and Talaromyces", published by Academic Press, 1979.

The present inventors named the present microorganism "*Penicillium paxilli* KAC-1843", and deposited it with The Fermentation Research Institute, the Agency of Industrial Science and Technology, Japan, as FERM P-8581 on Dec. 21, 1985. The KAC-1843 strain was transferred to the deposit under the Budapest Treaty as FERM BP-1199 on Nov. 6, 1986.

For the culturing of the microorganism of the present invention, the conventional procedure for culutirng mold is generally used. Any medium can be used as a culture medium, so long as it contains carbon sources, nitrogen sources, inorganic materials, etc. appropriately. As a carbon source, glucose, starch, glycerol, mannose, fructose, sucrose, molasses, etc. can be used alone or in combination. Furthermore, hydrocarbons, alcohols, organic acids, etc. can be used, depending on the assimilability of the microorganism. As a nitrogen source, inorganic or organic nitrogen-containing compounds such as ammonium chloride, ammonium sulfate, ammonium nitrate, sodium nitrate, urea, etc., and natural nitrogen-containing products such as peptone, meat extract, yeast extract, dry yeast, corn steep liquor, soybean meal, Casamino acid, etc. can be used alone or in combination. As an inorganic material, inorganic salts such as sodium chloride, potassium chloride, ferrous sulfate, zinc sulfate, manganese sulfate, cupric sulfate, calcium carbonate, potassium dihydrogen phosphate, dipotassium hydrogen phosphate, etc. can be used. Furthermore, organic or inorganic materials capable of promoting the production of UCY1003 such as biotin, vitamins, etc. can be used, if required.

Culturing can be carried out either by liquid culture or by solid culture, but usually liquid culture, particularly, submerged culture with stirring is used. Culturing temperature is 20° to 35° C., preferably 23° to 28° C. It is desired to control the pH of the medium to 4–10, particularly 5–7, with aqueous ammonia, an aqueous ammonium carbonate solution, etc. during the culturing. Usually after 1 to 7 days of liquid culture, the desired substance is formed and accumulated in the culture broth. When the yield reaches a maximum in the culture liquor, culturing is discontinued, and the desired substance is isolated and purified from the culture broth.

For the isolation and purification of UCY1003 from the culture broth, the ordinary method for isolating a microbial metabolite from its culture broth can be utilized. For example, the culture broth is separated into the culture filtrate and the microbial cells. The microbial cells are extracted with a solvent capable of dissolving the present substance such as chloroform, acetone, etc., and the extract is concentrated under reduced pressure to remove the solvent therefrom. The residue is dissolved in water. The aforesaid culture filtrate and the aqueous solution are passed through a column packed with a non-ionic porous resin, for example, Diaion HP-20 (made by Mitsubishi Kasei Kogyo Co., Ltd., Japan) and then the adsorbed active component is eluted with methanol, acetone, etc. The eluate is concentrated and the concentrate is adjusted to pH 2–4 with an acid such as sulfuric acid, etc. to precipitate UCY1003.

Crude UCY1003 obtained as the precipitate is dissolved in a solvent such as ethyl acetate, toluene, etc. The solution is subjected to various kinds of chromatography using silica gel, etc. to elevate the purity, and a pure product can be obtained by crystallization from chloroformethyl acetate, etc.

The amount of UCY1003 in the culturing and purification can be analyzed by thin layer chromatography, etc. That is, UCY1003 has an Rf value of 0.19 in thin layer chromatography using the silica gel plate (Art 5715 made by Merck Co.) and chloroform:ethyl acetate (3:1) as a developing solvent.

UCY1003 has analgesic, hypotensive and antifungal activities and is useful as an effective ingredient of an analgesic agent, a hypotensive agent or an antifungal agent for human beings. When a medicine containing UCY1003 as an effective ingredient is used as an analgesic agent or a hypotensive agent, such a medicine is usually orally administered to a patient in a dose of 3–10 mg/kg/day as UCY1003. When the medicine is used as an antifungal agent, such a medicine is usually orally administered to a patient in a dose of 8–20 mg/kg/day as UCY1003. The above daily dose is appropriately divided so that the medicine may be orally administered 1 to 3 times a day as an analgesic agent or a hypotensive agent and 2 to 4 times as an antifungal agent.

UCY1003 may be administered in the form of tablets, granules, powder, capsules, syrup, ointment, cream, injection or the like prepared in a conventional manner depending upon the purpose and method of administration. For example, in a tablet form, tablets containing 50–250 mg of active ingredient per tablet are preferably used. In preparing tablets, an excipient (e.g., lactose, glucose, sucrose, mannitol, methylcellulose, etc.), a disintegrator (e.g., starch, sodium alginate, carboxymethylcellulose calcium, crystalline cellulose, etc.), a lubricant (e.g., magnesium stearate, talc, etc.), a binder (e.g., gelatin, polyvinyl alcohol, polyvinyl pyrrolidone, hydroxypropylcellulose, methylcellulose, etc.), a surfactant (e.g., fatty acid ester of sucrose, fatty acid ester of sorbitol, etc.) and the like are used in a conventional manner. In preparing granules, an excipient (e.g., lactose, sucrose, etc.), a disintegrator (e.g., starch, etc.), a binder (e.g., gelatin) and the like are used in a conventional manner. In preparing powder, an excipient (e.g., lactose, mannitol, etc.) and the like are used in a conventional manner. In a capsule form, capsules containing 50–150 mg of active ingredient per capsule are preferably used. In preparing capsules, gelatin, water, sucrose, Arabic gum, sorbitol, glycerin, crystalline cellulose, magnesium stearate, talc, etc. are used in a conventional manner. In preparing syrup, sugar (e.g., sucrose, etc.), water, ethanol, etc. are used in a conventional manner.

In preparing ointment, ointment base (e.g., vaseline, liquid paraffin, lanolin, macrogol, etc.), emulsifying agent (e.g., sodium lauryl sulfate, benzalkonium chloride, monoaliphatic acid ester of sorbitan, carboxymethylcellulose sodium, Arabic gum, etc.) and the like are used in a conventional manner. In preparing injection, solvent (e.g., water, physiological sodium chloride solution, vegetable oil such as olive oil and peanut oil, ethyl oleate, propylene glycol, etc.), a solubilizing agent (e.g., sodium benzoate, sodium salicylate, urethane, etc.), a tonicity agent (e.g., sodium chloride, glucose, etc.), a preservative (e.g., phenol, cresol, an ester of p-oxybenzoic acid, chlorobutanol, etc.), an antioxidant (e.g., ascorbic acid, sodium pyrosulfite, etc.) and the like are used in a conventional manner.

Pharmacological activities of UCY1003 are shown by the following experiments.

Experiment 1 (Analgesic Activity)

In this experiment, 4 male dd mice wieghing 20±1 g were used as one group for examination of analgesic activity. Sixty minutes after intraperitoneal administration of UCY1003 to each animal, 0.2 ml of a 0.7% acetic acid solution was intraperitoneally administered to the animal. Starting 10 minutes after the administration of acetic acid, the number of writhes occurred in 5 minutes was counted. Inhibition ratio in comparison with control group was calculated by the following equation. The results are shown in Table 1. ED$_{50}$ value was calculated in accordance with Litchfield and Wilcoxon.

$$\text{Inhibition ratio} = \frac{A - B}{A} \times 100$$

A: Average number of writhes of control group
B: Average number of writhes of test group A: Average number of writhes of control group
B: Average number of writhes of test group

TABLE 1

| Dose (mg/kg, i.p.) | N | Inhibition Ratio (%) | ED$_{50}$ (mg/kg, i.p.) |
|---|---|---|---|
| 100 | 4 | 95 | |
| 50 | 4 | 83 | |
| 25 | 4 | 52 | 17 |
| 10 | 4 | 52 | |
| 5 | 4 | 17 | |

Experiment 2 (Hypotensive Activity)

Male spontaneously hypertensive rats (SHR) of Okamoto-Aoki strain (body weight, 310–360 g) were used. Systolic blood pressure of conscious SHR was measured indirectly from the tail artery with a plethysmographic apparatus (Ueda Electric Works, USM-105R). Test compound UCY1003 was suspended in 0.3% sodium carboxymethylcellulose (CMC) solution and was intraperitoneally administered in a volume of 2 ml per kg of body weight.

As indicated in Table 2, the compound caused hypotension at a dose of 100 mg/kg.

TABLE 2

| Dose (mg/kg, i.p.) | N | before | after (90 min) | Difference[2] |
|---|---|---|---|---|
| 100 | 3 | 187 ± 3[1] | 142 ± 9 | 45 ± 8 |

Blood Pressure (mmHg)

TABLE 2-continued

| Dose (mg/kg, i.p.) | N | before | after (90 min) | Difference[2] |
|---|---|---|---|---|
| 50 | 3 | 195 ± 8 | 177 ± 14 | 18 ± 15 |

Blood Pressure (mmHg)

[1]mean ± S.E.
[2]difference in mmHg between the values measured before and 90 min. after administration.

Experiment 3 (Antifungal Activity)

Anti-bacterial activities of UCY1003 against various microorganisms measured by agar dilution method (pH 7) are shown in Table 3.

TABLE 3

| Test microorganisms | MIC (μg/ml) |
|---|---|
| *Staphylococcus aureus* ATCC 6538P | >100 |
| *Bacillus subtilis* No. 10707 | >100 |
| *Klebsiella pneumoniae* ATCC 10031 | >100 |
| *Salmonella typhosa* ATCC 9992 | >100 |
| *Escherichia coli* ATCC 26 | >100 |
| *Candida albicans* ATCC 10231 | >100 |
| *Saccharomyces cerevisiae* C-203 | 2 |

Experiment 4 (Acute Toxicity)

UCY1003 was intraperitoneally administered once to each animal of the test group consisting of 5 ddY mice. After the administration, the animals were observed for 14 days and deaths were noted. The LD$_{50}$ was determined by Beherns Kärber's method to be more than 200 mg/kg.

Certain specific embodiments of the present invention are illustrated by the following examples.

EXAMPLE 1

Penicillium paxilli KAC-1843 (FERM BP-1199) was used as a seed strain.

One loopful of the strain was inoculated in 50 ml of a seed medium having the following composition in a 300 ml-Erlenmeyer flask, and subjected to shaking culture at 25° C. for 48 hours.

Seed medium composition (in 1 l): 20 g of sucrose, 10 g of glucose, 20 g of powdery soybean cake, 10 g of corn steep liquor, 0.5 g of KH$_2$PO$_4$, 0.5 g of MgSO$_4$.7H$_2$O, 2 g of CaCO$_3$ (pH 6.5)

The seed culture broth was transferred in an amount of 5% by volume into 18 l of a fermentation medium having the following composition in a 30 l-jar fermenter, and cultured at 25° C. with aeration and stirring (rotation: 350 rpm, aeration: 18 l/min.)

Fermentation medium composition (in 1 l): 50 g of sucrose, 20 g of corn steep liquor, 0.5 g of KH$_2$PO$_4$, 0.5 g of MgSO$_4$.7H$_2$O, 5 g of CaCO$_3$ (adjusted to pH 7.0 with NaOH)

Culturing was conducted for 50 hours without controlling the pH of the medium. After the end of culturing, the medium was adjusted to pH 8.5 with NaOH, and 5 l of n-propanol was added thereto. Then, the culture broth was stirred for 30 minutes. By removing the microbial cells from the cultue broth by filtration, 20 l of the filtrate was obtained. The filtrate was adjusted to pH 6 with sulfuric acid, and then passed through a column filled with 1 l of nonionic porous resin (Diaion SP-207, trademark of a product made by Mitsubishi Kasei Kogyo Co., Ltd., Japan) to adsorb the active substance. After eluting the impurities therefrom with 5

1 of water and then with 5 l of methanol; the adsorbed active substance was eluted with 5 l of acetone. The acetone-eluted fractions were concentrated and the concentrate was adjusted to pH 3 with sulfuric acid to deposit a precipitate. The precipitate was dissolved in ethyl acetate, and toluene was added thereto. Then, the mixture was concentrated to remove ethyl acetate therefrom. The concentrated liquid was passed through a silica gel column to adsorb the active substance. Impurities were eluted therefrom with chloroform, and then the active substance was eluted with a mixture of chloroform:ethyl acetate (5:1). The active fractions were concentrated, whereby 1.5 g of needles of UCY1003 was obtained. Then, the crystals were dissolved in chloroform -ethyl acetate. By recrystallization at 4° C., white needles of purified UCY1003 were obtained.

EXAMPLE 2

Operations were carried out in the same manner as in Example 1, except that a fermentation medium having the following composition was used in place of the fermentation medium of Example 1, whereby 1.2 g of UCY1003 was obtained.
Fermentation medium composition (in 1 l): 50 g of soluble starch, 20 g of powdery soybean cake, 0.5g of KH$_2$PO$_4$, 0.5 g of MgSO$_4$.7H$_2$O, 5 g of CaCO$_3$ (adjusted to pH 7.0 with NaOH)

EXAMPLE 3 (Tablet)

UCY1003 (400 g), lactose (28 g) and carboxymethylcellulose calcium (18 g) are mixed, and 10% aqueous hydroxypropylcellulose (10 g) is added thereto. The mixture is kneaded, granulated and dried in a conventional manner to prepare granules. The granules are mixed with magnesium stearate (4 g). The mixture is compressed with a tableting machine having a punch (diameter: 9 mm) to obtain tablets (230 mg/tablet). Each tablet contains 200 mg of UCY1003.

What is claimed is:
1. A substance UCY1003 having the following chemical structure:

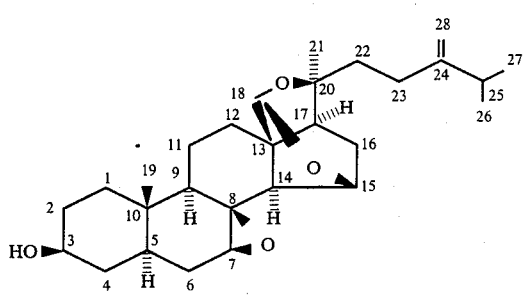

Figure 2:
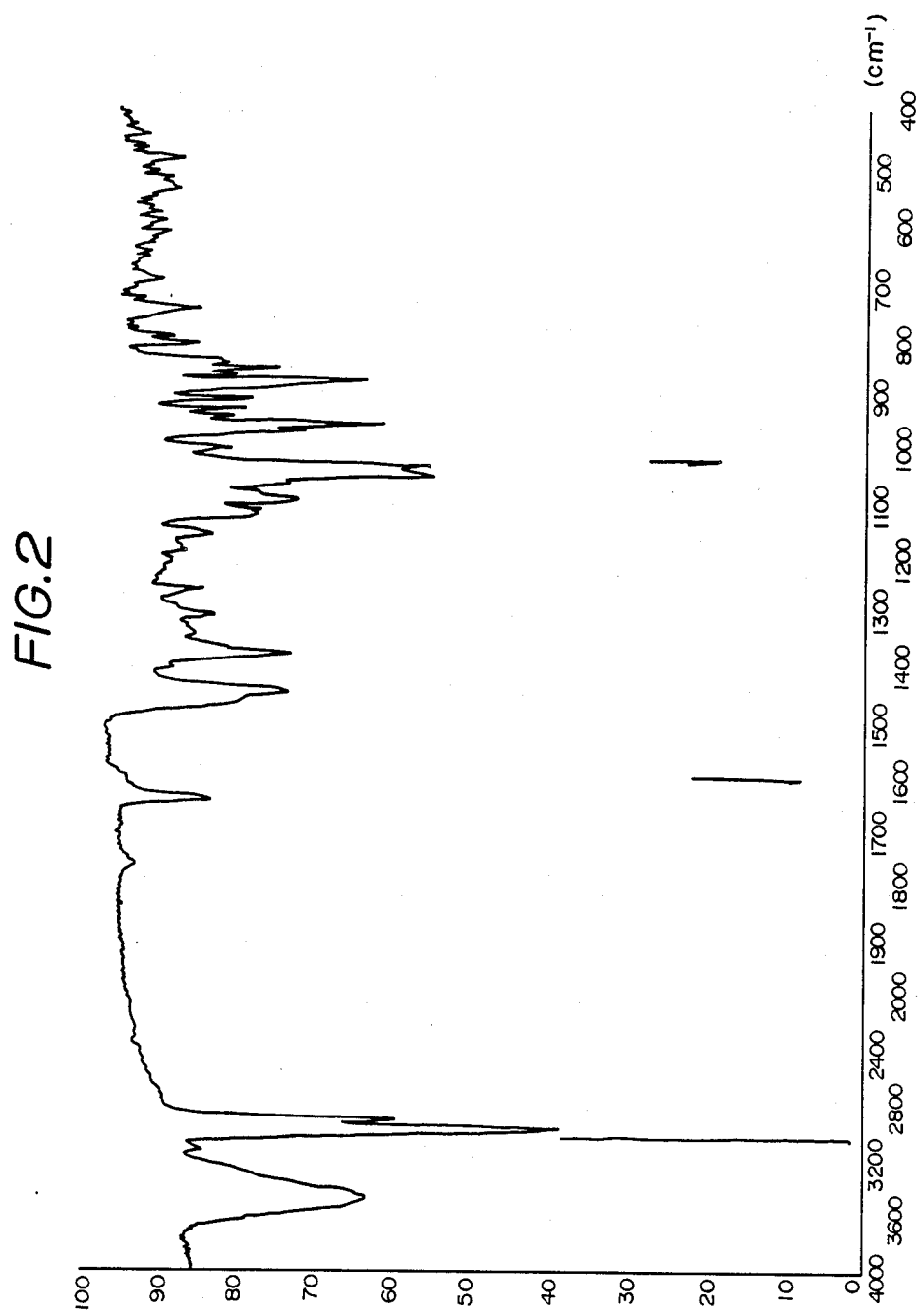
Figure 3:
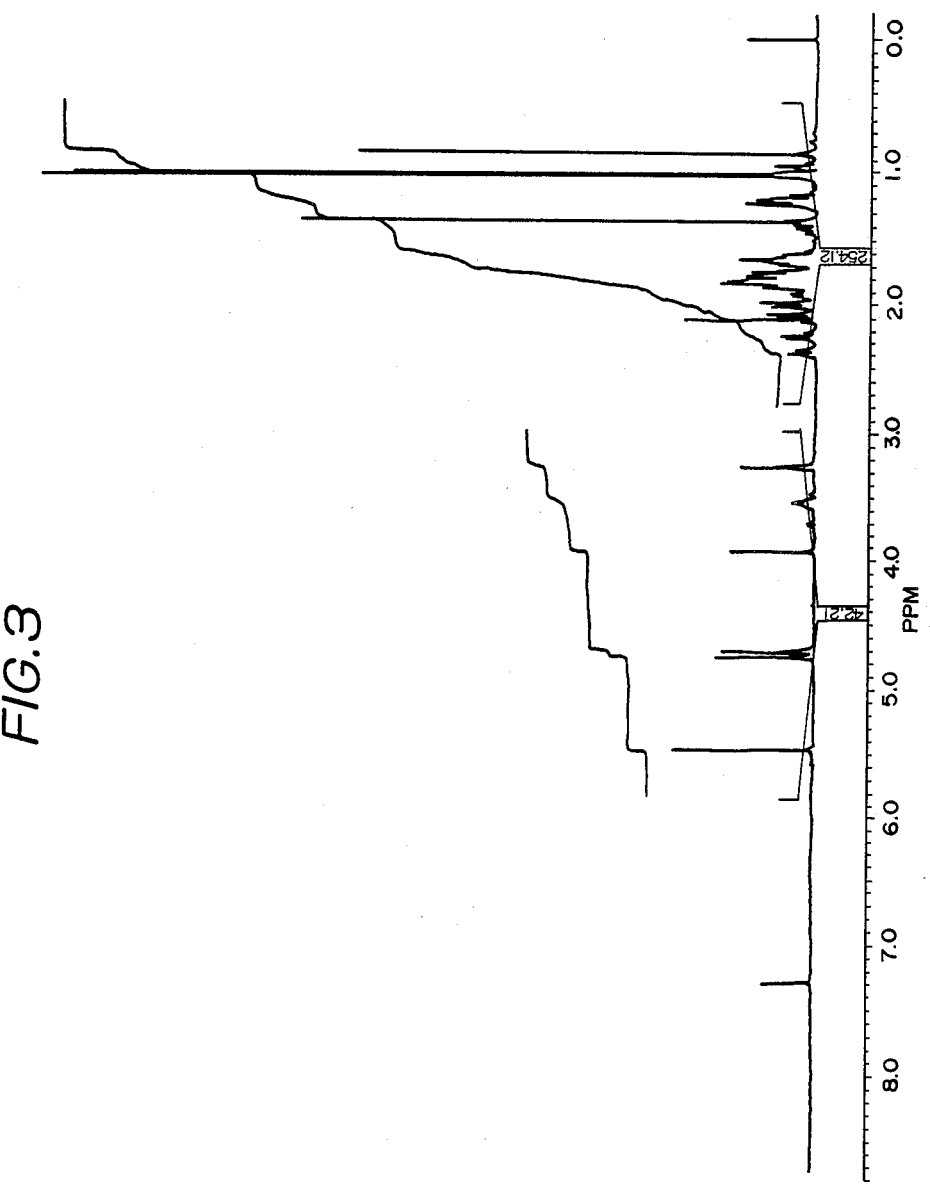
Figure 4:
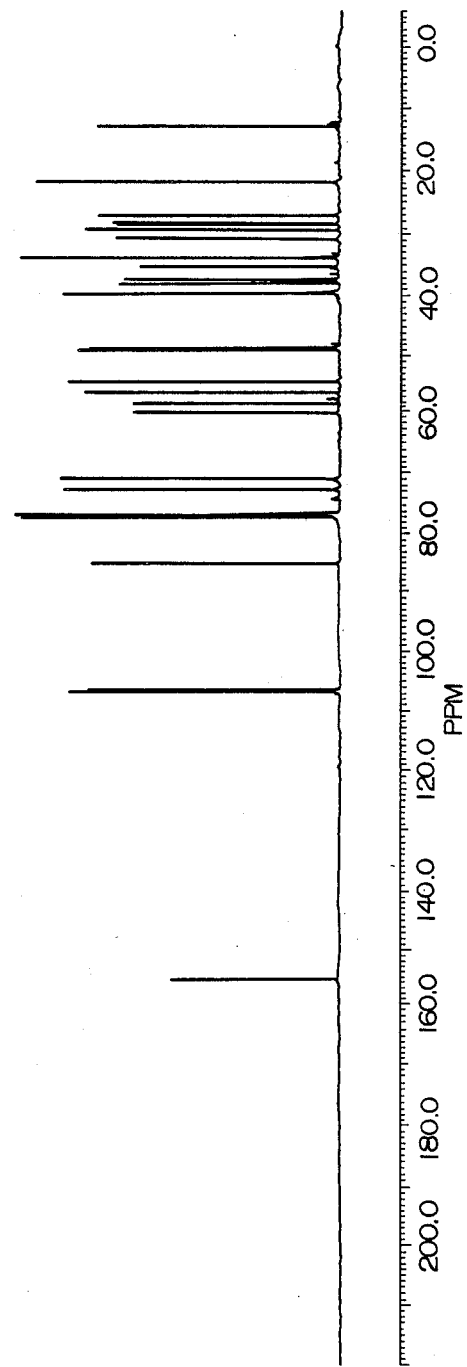

2. A substance UCY1003 defined by the following physicochemical properties
   (a) Molecular formula: $C_{28}H_{42}O_4$
   (b) Elemental analysis: C: 75.97%, H: 9.56%, N: 0%
   (c) Molecular weight: molecular weight of UCY1003 measured by EI mass spectrum method is 442, and the mass spectrum is shown in FIG. 1 (EI method)
   (d) Melting point 198.9° C.
   (e) Specific rotation: $[\alpha]_D^{25} = -60.8°$ (C 1.0, CHCl$_3$)
   (f) Ultraviolet absorption spectrum: only terminal absorption is shown
   (g) Infrared absorption spectrum: shown in FIG. 2 (KBr method)
   (h) PMR spectrum: shown in FIG. 3 (in CDCl$_3$)
   (i) CMR spectrum: shown in FIG. 4 (in CDC$_3$)
   (j) Solubility: readily soluble in methanol, ethanol, chloroform and acetone; soluble in ethyl acetate, toluene, and water; and sparingly soluble in hexane
   (k) State of the substance: white needles, neutral substance
   (l) Color reaction: positive to iodine reaction

* * * * *